(12) United States Patent
DeMars et al.

(10) Patent No.: US 6,225,443 B1
(45) Date of Patent: *May 1, 2001

(54) **CYTOTOXIC T LYMPHOCYTE EPITOPES OF THE MAJOR OUTER MEMBRANE PROTEIN OF *CHLAMYDIA TRACHOMATIS***

(75) Inventors: Robert I. DeMars; Seon-Kyeong Kim, both of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/551,510

(22) Filed: Apr. 17, 2000

Related U.S. Application Data

(63) Continuation-in-part of application No. 09/314,742, filed on May 19, 1999.

(51) Int. Cl.$^7$ .................................................. C07K 16/00
(52) U.S. Cl. ..................... 530/328; 530/328; 530/350; 530/300; 435/6; 435/320.1; 435/240.2; 435/91.2; 536/23.1; 536/24.32
(58) Field of Search .................... 530/350, 300, 530/328; 435/6, 320.1, 240.2, 91.2; 536/23.1, 24.32

(56) References Cited

U.S. PATENT DOCUMENTS

| 5,770,714 | 6/1998 | Agabian et al. ................ 536/23.1 |
| 5,821,055 | 10/1998 | Agabian et al. ................ 435/6 |
| 6,001,372 | 12/1999 | DeMars et al. ................ 424/263.1 |

FOREIGN PATENT DOCUMENTS

| 192033 | 8/1985 | (EP) . |
| WO97/46256 | * 12/1997 | (WO) . |
| WO 98/50074 | 11/1998 | (WO) . |

OTHER PUBLICATIONS

Alignment.*

L. Ortiz et al., Chlamydia Trachomatis Major Outer Membrane Protein (MOMP) Epitopes That Activate HLA Class II–Restricted T Cells From Infected Humans, 157 J. Immunol. 4554–4567 (1996).

E. Peterson et al., The Major Outer Membrane Protein Nucleotide Sequence Of Chlamydia Trachomatis, Serovar E, 18 Nuc. Acid. Res. 3414 (1990).

M. Holland et al., Synthetic Peptides Based On Chlamydia Trachomatis Antigens Identify Cytotoxic T Lymphocyte Responses In Subjects From a Trachoma–Endemic Population, 107 Clin. Exp. Immunol. 44–49 (1997).

D. Zhang et al., DNA Vaccination With The Major Outer–Membrane Protein Gene Induces Acquired Immunity To Chlamydia Trachomatis (Mouse Pneumonitis) Infection, 176 J.I.D.. 1035–1040 (1997).

S. Kim et al., HLA Class I–Restricted, $CD8^+CTL$ Specific For Chlamydia Trachomatis MOMP Are Induced In Genital Tract Infections, 1998 Autumn Immunology Conference (1998).

H. Rammensee, et al., MHC Ligands And Peptide Motifs: First Listing, 41 Immunogen. 178–228 (1995).

S. Kim et al., Induction of HLA Class I–Restricted $CDS^+$ CTLs Specific For The Major Outer Membrane Protein Of *Chlamydia trachomatis* in Human Genital Tract Infections, 162 J. Immunol. 6855–6866 (1999).

J. Altman et al., Phenotypic Analysis Of Antigen–Specific T Lymphocytes, 274 Science 94–96 (1996).

V. Engelhard, How Cells Process Antigens, Scientific American, pp. 54–61 (Aug., 1994).

* cited by examiner

*Primary Examiner*—Karen Cochrane Carlson
*Assistant Examiner*—Hope A. Robinson
(74) *Attorney, Agent, or Firm*—Quarles & Brady LLP

(57) ABSTRACT

Disclosed herein are 9 amino acid-long peptides from the major outer membrane protein (MOMP) of *Chlamydia trachomatis* serovar E. These peptides activate CD8+ cytotoxic T-lymphocytes in human infections that are potentially important for resolution of infection and protection against disease. Thus, the peptides, as well as DNA coding for them, are intended for use in vaccination of humans. Also, they are useful in connection with diagnostic tests.

2 Claims, No Drawings

SEQUENCE LISTING

```
<160> NUMBER OF SEQ ID NOS: 8

<210> SEQ ID NO: 1
<211> LENGTH: 9
<212> TYPE: PRT
<213> ORGANISM: Chlamydia trachomatis

<400> SEQUENCE: 1

Ser Leu Asp Gln Ser Val Val Glu Leu
 1               5
```

<210> SEQ ID NO: 2
<211> LENGTH: 9
<212> TYPE: PRT
<213> ORGANISM: Chlamydia trachomatis

<400> SEQUENCE: 2

Arg Leu Asn Met Phe Thr Pro Tyr Ile
 1               5

<210> SEQ ID NO: 3
<211> LENGTH: 9
<212> TYPE: PRT
<213> ORGANISM: Chlamydia trachomatis

<400> SEQUENCE: 3

Asn Met Phe Thr Pro Tyr Ile Gly Val
 1               5

<210> SEQ ID NO: 4
<211> LENGTH: 9
<212> TYPE: PRT
<213> ORGANISM: Chlamydia trachomatis

<400> SEQUENCE: 4

Asn Ala Ala Cys Met Ala Leu Asn Ile
 1               5

<210> SEQ ID NO: 5
<211> LENGTH: 9
<212> TYPE: PRT
<213> ORGANISM: Chlamydia trachomatis

<400> SEQUENCE: 5

Asp Ala Asp Lys Tyr Ala Val Thr Val
 1               5

<210> SEQ ID NO: 6
<211> LENGTH: 9
<212> TYPE: PRT
<213> ORGANISM: Chlamydia trachomatis

<400> SEQUENCE: 6

Trp Gln Ala Ser Leu Ala Leu Ser Tyr
 1               5

<210> SEQ ID NO: 7
<211> LENGTH: 9
<212> TYPE: PRT
<213> ORGANISM: Chlamydia trachomatis

<400> SEQUENCE: 7

Ala Ser Leu Ala Leu Ser Tyr Arg Leu
 1               5

<210> SEQ ID NO: 8
<211> LENGTH: 9
<212> TYPE: PRT
<213> ORGANISM: Chlamydia trachomatis

<400> SEQUENCE: 8

Leu Ala Leu Ser Tyr Arg Leu Asn Met
 1               5

CYTOTOXIC T LYMPHOCYTE EPITOPES OF THE MAJOR OUTER MEMBRANE PROTEIN OF *CHLAMYDIA TRACHOMATIS*

CROSS REFERENCES TO RELATED APPLICATIONS

This is a continuation-in-part of U.S. Ser. No. 09/314,742 filed May 19, 1999.

This invention was made with United States government support awarded by the following agency: NIH A134617. The United States has certain rights in this invention.

BACKGROUND OF THE INVENTION

The present invention relates to nine amino acid-long peptides of the major outer membrane protein ("MOMP") from *Chlamydia trachomatis* ("Ct"). These peptides activate human cytotoxic T-lymphocytes ("CTLs").

Ct is an intracellular bacterium that is the leading cause of preventable infectious blindness (ocular trachoma) in the developing world and of sexually transmitted disease ("STD") in the United States and certain other parts of the developed world. The estimated annual incidence of Ct-caused STD is in the millions. While most Ct-caused disease can be treated with antibiotics, untreated or inadequately treated infections result in hundreds of thousands of cases of pelvic inflammatory disease each year in the United States, alone.

Adverse outcomes of pregnancy, ectopic pregnancy and tubal infertility are among the consequences of genital tract infections with Ct. Moreover, apparent clearance of infection by a given serovar (serologically distinct strain of Ct) can be followed by the infection becoming latent and prolonged or by re-infection. This is important because much Ct-caused pathology results from tissue-damaging inflammatory responses of the immune system that are triggered by repeated or prolonged exposures to the whole organism. Therefore, there is a need for improved means to prevent primary infections.

A great deal of effort has been put into developing a vaccine against diseases caused by Ct infections. While whole inactivated organisms are often used as a vaccine to immunize humans, such a vaccine is not desirable in the case of Ct because certain proteins expressed by Ct, such as chlamydial heat shock proteins, induce pathological immune responses rather than protective immune responses and, thus, contribute to disease. As a result, much vaccine-related activity in chlamydial research is centered on developing a "subunit vaccine" that consists only of Ct protein antigens or specific parts of the proteins that elicit protective immune responses in vaccinees. The fact that B-cell responses (neutralizing antibody) to Ct MOMP protect mice from Ct-caused disease has led to a prevailing theory that MOMP, when used to vaccinate humans, might also induce protective B- and T-cell responses.

However, using whole MOMP as a vaccine is not a good solution. Whole MOMP is too difficult to isolate from natural Ct cultures in large quantities that are sufficiently pure for use in mass vaccination. Larger quantities of recombinant MOMP could theoretically be produced in *E. coli,* but the chemical properties (e.g. insolubility except in detergents) impede its large scale preparation as a non-toxic vaccine. Furthermore, use of whole MOMP has too much risk of adverse side effects.

Consequently, emphasis has been given to developing a subunit vaccine that contains multiple B- and T-cell "epitopes" in MOMP, i.e. short antigenic MOMP peptides that are recognized by B and T cells. To achieve that goal, it is critical to identify which MOMP peptides are recognized by B and T cells of infected people. To date, there have been a number of reports regarding attempts to develop vaccines based on single or multiple MOMP peptide fragments, where the focus is on raising Th—cell and/or B-cell responses (mostly in mice, but in some cases, in humans). See H. Su et al., 172 J. Exp. Med. 203–212 (1990) (serovar A); J. Allen et al., 147 J. Immunol. 674–679 (1991) (serovar B); M. Ishizaki et al., 60 Infect. & Immun. 3714–3718 (1992) (serovars B, C); G. Zhong et al., 151 J. Immunol. 3728–3736 (1993) (serovar B). L. Ortiz et al. 157 J. Immunol. 4554–4567 (1996)(serovar E) and U.S. Pat. No. 6,001,372 (serovar E). The disclosure of these publications and of all other publications referred to herein are incorporated by reference as if fully set forth herein.

The 371 amino acid sequence of mature MOMP of Ct serovar E, a common cause of genital tract infections, is also disclosed in L. Ortiz et al. 157 J. Immunol. 4554–4567 (1996). The naturally occurring DNA coding sequence of serovar E-MOMP is disclosed in E. Peterson et al., 18 Nuc. Acids. Res. 3414 (1990). MOMP is a transmembrane protein and comprises more than 60% of all outer membrane proteins of Ct.

Sequence analysis of MOMP from various sources has revealed that differences in amino acid sequence confined to surface-exposed "variable segments" (VSs) of MOMP account for the serological specificity of different serovars and, also, for differences in Th-cell responses to different isolates. See M. Ishizaki et al., 60 Infect. & Immun. 3714–3718 (1992). On the other hand, membrane-embedded regions of MOMP contain amino acid sequences that are conserved among different Ct serovars, and hence the name, "constant segments (CSs)". Notably, a majority of Th-cell epitopes is located in MOMP CSs in contrast to B-cell epitopes, which are exclusively located in MOMP VSs.

T cells recognize their peptide epitopes only when they are presented on the surface of other cells in association with a particular kind of HLA (human leukocyte antigen; human MHC (major histocompatibility complex)) molecules. Different kinds of HLA molecules present different peptide epitopes. A complicating matter in vaccination of humans is the fact that HLA genes are extremely polymorphic in the human population. That is, different individuals express different HLA types, and a T-cell epitope that elicits immune responses in some individuals may not do so in others. This is a particularly troubling problem for those seeking to develop vaccines for the human population in general. Consequently, there remains a need to identify many different peptide epitopes presented by diverse HLA allotypes that elicit immune responses in the majority of population. Such a set of epitopes can then be used to create a "cocktail" type sub-unit vaccine containing multiple T-cell epitopes as well as B-cell epitopes.

Recently there has been a description in M. Holland et al., 107 Clin. Exp. Immunol. 44–49 (1997) of two MOMP peptides that stimulated limited CTL responses in HLA-B8+ or HLA-B35+ individuals who had experienced trachoma, an eye infection with Ct. However, only two of twelve HLA-B8+ subjects responded to the peptide therefor, and only one of thirteen HLA-B35+ subjects responded to the peptide therefor. These CTLs showed low lytic activity against targets incubated with the peptides and ability of the CTLs to lyse Ct-infected target cells was not examined.

Apart from vaccine utility, it is desirable to find CTL epitopes that can be used as components of diagnostic tests (e.g. to confirm the presence of the disease once a positive test result has been obtained using conventional tests).

In summary, the identification of human CTL epitopes is needed to design a sub-unit vaccine, and is of interest in developing diagnostic tests.

BRIEF SUMMARY OF THE INVENTION

Our invention concerns a specific type of T cell responses, i.e. cytotoxic T lymphocyte (CTL) responses, in human genital tract infections with Ct. CTLs have been well documented as critical players in providing protection against infections with intracellular pathogens, including viruses, bacteria, fungi and parasites. CTLs exert their protective effector function by specifically recognizing an infected cell and secreting cytotoxic molecules that lead to the lysis and death of the infected cell, as well as the pathogens residing inside the cell. CTL recognition of an infected cell requires presentation on the cell surface of short peptide epitopes derived from proteins of the pathogens in association with HLA class I molecules.

Such peptides are generated by "the antigen processing machinery" of the infected cell, which includes cytosolic proteases and the transporter molecules that move the peptides into a cellular compartment where they can bind to HLA class I molecules. It should be noted that only a fraction of peptides generated by a cell are indeed capable of activating CTLs. This is because each CTL expresses at the cell surface T-cell receptors that are specific for a single kind of HLA class I-peptide complex. It is only when the T-cell receptors bind to correct HLA class I-peptide complexes displayed by an infected cell that the CTLs become activated and capable of killing the infected cell.

In one aspect the invention provides a peptide of 9 to 10 amino acid sequences comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

In another aspect, the invention provides nucleotide sequences for expressing such peptides. Such nucleotide sequences are, for example, preferably those that incorporate the applicable coding portion for the fragment of the natural MOMP gene, as described in E. Peterson et al., 18 Nuc. Acids. Res. 3414 (1990). Alternative codons that express the same amino acids may also be used.

In yet another form, the invention discloses vaccine candidates containing such peptides or nucleotide sequences. The vaccines are designed to induce cytotoxic T lymphocyte ("CTL") responses in humans so as to increase the capacity of humans to resist adverse diseases resulting from *Chlamydia trachomatis* ("Ct") infection.

As noted above, activation of CTLs requires specific recognition of pathogen-derived short peptides (e.g. nine and ten mers are highly preferred in our case) which have bound to specific kinds of HLA class I molecules. Moreover, the CTL epitopes can be used to detect MOMP peptide-specific CTLs in peripheral blood of infected people and thus provides a diagnostic tool.

Detection of the MOMP-specific CTLs can be accomplished in two basic ways. First, a reagent called a "HLA class I tetramer" incorporating the invention can be used to enumerate MOMP peptide-specific CTLs in blood samples directly upon their removal from subjects being diagnosed for infection. Second, the CTLs in such blood samples can first be activated with our invention to proliferate in vitro and then be enumerated with the use of tetramers.

If a conventional diagnostic test based on Th-cell or B-cell antigenic response provides a negative initial result, false negatives and true positives can be diagnosed by checking blood samples using direct detection or activation followed by detection of the CTLs as the indicator. Thus, the invention can provide a method for diagnosing whether a human has been infected with Ct. Moreover, since the numbers of CTLs may reflect the stage of the infection and progress of pathogenesis, enumeration of the CTLs provides a diagnostic basis for prognosis.

The basic tools are HLA class I tetramers, each kind of tetramer incorporating just one or another of the eight claimed peptides that comprise the invention in combination with the specific kind of HLA class I molecules that binds the peptide. Each kind of tetramer binds to only those CTLs that recognize and are activated by the peptide used to make that kind of tetramer. The tetramers are fluorescently tagged in a way that allows each cell that binds a tetramer to be counted with a device called a flow cytometer. Thus, creation of the powerful tools called tetramers depends on identifying peptide epitopes that are recognized by CTLs; the invention identifies eight such epitopes.

The advantages of the present invention therefore include providing:

(a) peptides that can activate human CTLs;

(b) genes coding for such peptides;

(c) sub-unit vaccines based on such peptides; and (d) diagnostic tests using such materials.

These and still other advantages of the present invention will be apparent from the description which follows. The following description is merely of the preferred embodiments. Thus, the claims should be looked to in order to understand the full scope of the invention.

DETAILED DESCRIPTION

General Overview

We have discovered that HLA class I-restricted $CD8^+$ CTLs specific for the Ct MOMP are present in the peripheral blood of humans who acquired genital tract infections with the organism. Three HLA-A2-restricted epitopes, two HLA-B51-restricted epitopes, one HLA-B62-restricted epitope, and two HLA-B35 epitopes have been identified in MOMP of Ct serovar E, which is a common cause of genital tract infections. One of the eight epitopes spans a variable (non-conserved) segment of MOMP and is likely a serovar E-specific epitope that is recognized only by subjects infected with serovar E (SEQ ID NO 1). The other seven epitopes are localized in conserved segments (SEQ ID NOs 2–8) and are recognized by CTLs isolated from all infected subjects tested, regardless of their infecting serovars.

The relevance of the CTLs we detected to genital tract infections with Ct is attested to in at least three ways. (a) CTLs that recognize peptides from MOMP of Ct do not respond to peptides derived from the corresponding peptides of MOMP from the related common human pathogen *Chlamydia pneumoniae,* which causes different diseases. (b) HLA class I tetramers made with claimed peptides bind to significant numbers of CD8+ T cells when the cells are derived from Ct-infected subjects but not from uninfected subjects. (c) ME180 and HeLa human cervical epithelial cells productively infected with Ct are lysed by MOMP peptide-specific CTLs; uninfected cells are not lysed. These cell lines are the type of cell that is naturally infected with Ct in the female genital tract and our results indicate that such infected cells could be lysed by the MOMP-specific CTLs in vivo.

Materials And Methods

Human subjects who had recent symptomatic genital tract infections with *Chlamydia trachomatis* ("Ct") were recruited. All the infected STD subjects were treated with an oral dose of azithromycin upon confirmation of Ct infection. HLA-A2+ purportedly uninfected control subjects were recruited from the similar age group. Control subjects had been sexually active, but lacked previous history of genital tract infections with Ct.

HLA class I typing was performed by PCR-sequence specific primer amplification, using Class I ABC SSP Unitray kit (Pel-Freez Clinical Systems, Brown Deer, Wis.).

B lymphoblastoid cell lines (LCLs) were established from human subjects by transformation of peripheral blood mononuclear cells ("PBMCs") with Epstein-Barr Virus. HLA class-I mutant cell lines used as targets in CTL assays were derived from LCL 721. Mutants LCL.45 and LCL.19 were derived by mutagenizing LCL 721 with gamma rays and by using complement plus appropriate antibodies to select for HLA deletion mutants. Both LCLs.45 and .19 have the HLA-A2 and -B51 loci.

Further mutagenesis of LCL.45 produced mutant LCL.144, which is HLA-A-null due to a homozygous deletion at the locus; HLA-B51 remains intact. Similarly, HLA-B-null mutant LCL.53 was derived from LCL.19 as a result of intragenic deletion at the B locus but retains HLA-A2. LCLs were cultured at 37° C., in humidified 5% $CO_2$ in '2/1 RPMI'; RPMI 1640 (85%) supplemented with fetal calf serum (5%), defined/supplemented calf serum (10%), 25 mM HEPES, 44 mM $NaHCO_3$, 2 mM L-glutamine, 100 U/ml penicillin and 100 μg/ml streptomycin sulfate.

ME180 and HeLa human epithelioid carcinoma cells were used as a model for female genital tract epithelial cells that support the growth of Ct. ME180 was typed to be HLA-A1, -A32, -B8 and -B44 and HeLa was typed to be HLA-A3, -A68 and -B70 according to PCR-based typing (Tissue Typing Laboratory, University of Wisconsin, Madison, Wis.). ME180 cells were cultured in MEM containing 10% fetal calf serum, 100 μM non-essential amino acids, 25 mM HEPES, 44 mM $NaHCO_3$, 100 U/ml penicillin and 100 μg/ml streptomycin sulfate. ME180 cells expressing an HLA-A1 (ME180[A1]), HLA-A2 (ME180[A2]), or HLA-B51 transgene (ME180[B51]) were prepared by introducing into ME180 cells the RSV.5neo vector carrying the genomic HLA-A*0101, HLA-A*0201, or HLA-B51*01 gene, respectively. Stable transferent cells were selected for resistance to G-418 sulfate (500 μg/ml). The transferent cell lines permitted studies of CTLs specific for HLA class I molecules that were not initially present in the epithelial cells.

Human T cells were grown at 37° C. in humidified 5% $CO_2$ using DMEM containing 4.5 g/L glucose and supplemented with 10% pooled AB-negative human serum, 100 μM non-essential amino acids, 25 mM HEPES, 44 mM $NaHCO_3$, 2 mM L-glutamine, 100 U/ml penicillin and 100 μg/ml streptomycin sulfate. When needed, recombinant human IL-2 (rhIL-2) was added at 25 U/ml. Human serum was purchased from Pel Freez (Brown Deer, Wis.), and bovine sera were purchased from Hyclone Laboratories (Logan, Utah). All tissue culture media and reagents were purchased from Gibco-BRL (Grand Island, N.Y.). All other chemicals were purchased from Sigma (St. Louis, Mo.).

Peptide Synthesis

Nine-mer peptides in accordance with SEQ ID NOs: 1–8 possessing "binding motifs" (amino acid residues at the second and ninth positions that are required for peptide binding to HLA class I) for HLA-A2 (or HLA-B51 or HLA-B62 or HLA-B35) were identified in the mature Ct serovar-E MOMP sequence. C. pneumoniae MOMP peptides were made according to the published amino acid sequences.

Peptides were synthesized at the University of Wisconsin Biotechnology Center (Madison, Wis.) by F-moc chemistry. Identities of peptides were confirmed by amino acid analysis and matrix-assisted laser desorption/ionization mass spectrometry. Lyophilized peptides were dissolved in DMSO at 20 mM, aliquotted and stored at −80° C. Peptides were diluted to 4 mM with serum-free culture medium and used at desired final concentrations.

Ct MOMP peptides that can bind to HLA-A2 molecules were identified by their ability to increase the expression of HLA-A2 on the surface of TAP-deficient mutant cell line LCL.174. Briefly, LCL.174 was plated in a round-bottomed 96-well plate at 200,000 cells/well in 200 μl of 2/1 RPMI together with 50 μM of peptide and incubated overnight at 37° C. The cells were then stained with HLA-A2-specific monoclonal antibody, BB7.2 (ATCC, Rockville, Md.), followed by fluorochrome ("FITC")-conjugated goat anti-mouse IgG. Fluorescence intensity was analyzed by flow cytometry. Influenza virus matrix M1 protein peptide, FluMP58, is a known HLA-A2-presented CTL epitope and used as a positive control. Hepatitis B virus envelope antigen peptide, HBenvAg125, does not bind to HLA-A2 and was used as a negative control.

Stimulation Of CTLs

PBMCs were prepared from ~30 ml of heparinized peripheral blood obtained from human subjects by centrifugation over Ficoll-Hypaque (Sigma, St. Louis, Mo.). CD8+ cells were positively selected from freshly isolated PBMCs, or sometimes from PBMCs frozen in liquid $N_2$, using anti-CD8 magnetic microbeads according to the manufacturer's instructions (Milteny Biotec, Auburn, Calif.).

Negatively selected cells were resuspended in serum-free DMEM and plated in 500 μl aliquots into 48 well plates at $3\times10^6$ cells/well. After 2 hr at 37° C., 5% $CO_2$, non-adherent cells were removed by repeated washing, and adherent monocytes were incubated for 4 hr with 50 μM peptide and 5 μg/ml human β-2-microglobulin (Sigma, St. Louis, Mo.). After being washed with serum-free DMEM, each well received $1.5\times10^6$ CD8+ cells (>95% pure by flow cytometry) in 500 μl of DMEM containing 10% human serum supplemented with rhIL-7 (0.5 ng/ml; R&D Systems, Minneapolis, Minn.).

rhIL-2 was given at 25 U/ml after 2 days and twice a week thereafter by replacing half of the culture medium. On day 10, CTL cultures were restimulated at a responder to stimulator ratio of 5 with irradiated (5000 rad), autologous LCLs incubated with 20 μM peptide. Alternatively, LCL.174 incubated with 50 μM peptide was used to restimulate CTL cultures obtained from HLA-A2+ subjects. CTL assays were performed a week after restimulation as described below.

After initial characterization, peptide-stimulated CTLs could be frozen in medium that consisted of 30% human serum, 10% DMSO and 60% DMEM, and then thawed and restimulated for further analysis. Influenza virus matrix M1 protein peptide, FluMP58, was used as a positive control for in vitro stimulation of peptide-specific CTLs.

CTL Assays

Cytolytic activity of peptide-stimulated CTL cultures was assessed in [$^3$H]thymidine release assays or in [$^3$H]uridine release assays. Target LCLs ($3\times10^5$ cells/ml) were labeled overnight with [$^3$H]thymidine (2.0 Ci/mmol; New England Nuclear, Boston, Mass.) or with [$^3$H]uridine (25~30 Ci/mmol; Amersham, Arlington Heights, Ill.) at 10 μCi/ml, while in growth phase. After 1 hr incubation with or without 10 μM peptide, the target cells were washed three times to remove excess peptides. 5000 target cells were then plated in round-bottomed wells of 96-well plates along with different numbers of CTLs in a total volume of 200 μl of 2/1 RPMI to give desired effector (CTLs) to target ratios.

After 6 hr at 37° C., 100 μl of supernatant was harvested from each well, air-dried on glass fiber filters and counted in a liquid scintillation counter. Spontaneous release was determined for target cells in the absence of CTLs in medium alone. Maximal labeling was determined from equivalent wells by taking 100 μl after thoroughly mixing the contents of the wells. Maximal labeling was 3000–5000 cpm for [$^3$H]thymidine-labeled LCLs, and 6000–8000 cpm for [$^3$H] uridine-labeled LCLs. Spontaneous release was typically 5–10% of maximal labeling. When ME180 cells were used as targets, adherent cells were incubated overnight with radioactive labels as described above. Cells were then trypsinized and incubated for 1 hr with or without 10 μM peptide before being plated together with CTLs.

Maximal labeling was 5000–6000 cpm for [$^3$H] thymidine-labeled ME180 cells, and ~10,000 cpm for [$^3$H] uridine-labeled ME180 cells. Spontaneous release was usually 5–10% of maximal labeling.

Chlamydia-Infected Target Cells

Serovar E/UW-5 genital strain of Ct was grown in HeLa cells and purified by density gradient centrifugation. See generally our article at S. Kim et al., 162 J. Immunol. 6855–6866 (1999) (not prior art). The purified elementary bodies (EBs) were resuspended in SPG (sucrose-phosphate-glutamic acid buffer) and stored at −80° C. until use. Inclusion forming units (IFUs) of purified organisms were assayed on HeLa cells by indirect fluorescent-antibody staining as previously described.

ME180 and ME180[A2] cells were maintained without antibiotics until they were inoculated with Ct. Cells were seeded at 3×10$^5$ cells/well in a 12-well plate (Costar, New York, N.Y.) together with 10 μCi/ml [$^3$H]uridine. A 24-hour subconfluent monolayer was washed twice with PBS and inoculated with live, heat-killed or UV-killed EBs at a multiplicity of infection (MOI) of 10 (i.e. 10 IFUs per cell) in 500 μl of serum-free RPMI for 2 hr at 37° C. Heat-killed EBs were prepared by incubating them in a 56° C. water bath for 30 min, and UV light-inactivated EBs by exposing the organisms to a 30 W UV source (10 erg/sec, General Electric, Fairfield, Conn.) at a distance of 10 cm for 30 min.

Live EBs and killed EBs were used at equal dilutions. Inocula were removed by washing, and infected cells were cultured for 24 hr or for 48 hr in antibiotic-free RPMI 1640 containing 10% fetal calf serum before use in CTL assays. Uninfected cells were treated with medium alone, incubated for the same amount of time and used as a control in CTL assays.

CTL assays were performed with 5000 infected cells per well at an effector-to-target ratio of 50, as described above. Spontaneous release from infected cells was ~10% of maximum labeling at 24 hr post-infection and 15–20% at 48 hr post-infection; lysis of infected cells by CTLs was measured at these time points. At 72 hr post-infection, 60–70% of infected cells spontaneously lysed; this time point and later ones were excluded from our experiments. Spontaneous release from cells incubated with killed organisms remained similar (~10% of maximal labeling) up to 96 hr post-inoculation.

RESULTS

We chose to examine Ct MOMP-specific CTL responses restricted by HLA-A2, HLA-B51, HLA-B62, and HLA-B35, which are among the most common HLA class I allotypes found in various ethnic populations. Out of twenty-one Ct-infected subjects who enrolled in our research program, 14 (67%) were typed to be HLA-A2$^+$; 4 (20%) were typed to be HLA-B51$^+$; 5 (24%) were typed to be HLA-B62$^+$; and 3(14%) were typed to be BLA-B35+. All of the subjects yielded CTLs that responded to one or more MOMP peptides used to stimulate outgrowth of the CTLs in vitro. This, the peptides comprising our invention have the valuable attribute as vaccine components of eliciting CTL responses in at least a large proportion of infected subjects who have the kinds of HLA molecules that present the peptides to the immune system.

In making these determinations, amino acid sequences containing "binding motifs" for these HLA class I allotypes were identified in MOMP of Ct serovar E and were then synthesized and used to stimulate outgrowth of CD8$^+$ T cells obtained from peripheral blood of Ct-infected human subjects. Serovar E was chosen for the study, because it is one of the most common causes of human genital tract infections.

A total of 14 MOMP peptides possessing a proposed HLA-A2-binding motif were tested for their ability to bind to HLA-A2 molecules.

SEQ ID NOs: 1, 2 and 3 were identified as binders of HLA-A2 by means of binding studies with LCL.174 and were subsequently used for in vitro stimulation of CD8$^+$ cells obtained from HLA-A2$^+$ subjects. SEQ ID NO: 1 is an HLA-A2-presented CTL epitope that spans a variable segment of MOMP and is recognized only by subjects infected with serovar E. Thus, this epitope is most likely a serovar E-specific epitope. However, SEQ ID NOs: 2 and 3 are located in the constant segments of MOMP and are recognized by CTLs isolated from all 14 HLA-A2+ infected subjects tested, regardless of their infecting serovars.

Four synthetic peptides possessing binding motif for HLA-B51 were used in stimulation of CD8$^+$ cells from HLA-B51$^+$ subjects without performing preliminary peptide binding assays. Two of them, SEQ ID NOs: 4 and 5 were found to activate CTLs in HLA-B51+ STD subjects.

Similar experiments were performed with two peptides containing a binding motif for HLA-B62. One of the peptides, SEQ ID NO: 6, was recognized by three HLA-B62 subjects tested.

Similar experiments were performed with two peptides containing a binding motif for HLA-B35. Both peptides, SEQ ID NOs: 7 and 8, were recognized by two HLA-B62+ STD subjects tested.

To confirm that the MOMP peptide-specific CTLs described above were indeed elicited by genital tract infections with Ct, HLA-A2$^+$ uninfected subjects were recruited based on the lack of previous history of Ct genital tract infections. Their peripheral blood CD8$^+$ T cells were exposed in vitro to peptides SEQ ID NOs: 2 and 3 following the same protocol used for infected subjects. The cytolytic activity of CTL cultures was assessed in [$^3$H]thymidine release and [$^3$H]uridine release assays performed in parallel, using HLA-A2$^+$ LCL.53 as targets.

Five of six uninfected control subjects had no detectable CTL activity against the two MOMP peptides, while one had CTL populations specific for both peptides. The basic CTL stimulation protocol was functional in this experiment, as we detected influenza peptide-specific CTLs in all six control subjects. The MOMP-specific CTLs found in one of our control subjects may reflect previous asymptomatic infection with CT, which commonly occurs. Thus, it is noteworthy that asymptomatic Ct infection can be diagnosed in a seemingly uninfected person by in vitro stimulation of T cells with our inventions.

An additional control subject (HLA-A2+ and HLA-B51+) was tested with HLA-B51-restricted CTL epitopes, SEQ ID NOs: 4 and 5, as well as with HLA-A2-restricted CTL epitopes SEQ ID NOs: 2 and 3. None of these peptides stimulated CTLs in this subject.

We also addressed the possibility that the MOMP-specific CTLs we were detecting had actually been elicited by prior infection of our STD subjects with *Chlamydia pneumoniae* (Cpn). It was important to do this because immunological cross-reactivity of Ct MOMP and Cpn MOMP could confound the use of our invention as components of vaccines and as diagnostic tools. This was particularly important for CTL epitopes located in constant segments of MOMP, where Ct MOMP and Cpn MOMP share more than 70% sequence homology. Therefore, peptides of Cpn MOMP that correspond to our inventions (Ct MOMP CTL epitopes SEQ ID NOs: 2–5) were synthesized and CTL assays were performed with them. We found that when CTLs were elicited with given Ct MOMP peptides, target cells exposed to the same Ct MOMP peptides were lysed by the CTLs but the CTLs did not lyse the same target cells exposed to the corresponding Cpn peptides. Thus, the CTLs we detected in STD subjects are not cross-reacting CTLs that have resulted from Cpn infections but are specific for genital tract infections with Ct.

In order to show that the CTLs detected and elicited with our invention could actually interact with infected cells in vivo, we determined whether the CTLs could lyse human female genital tract epithelial cells that presented appropriate MOMP peptides. This demonstration was made in three stages. First, we exposed PBMCs from HLA-A2+ and -B51+ Ct-infected STD subjects to peptides SEQ ID NOs: 2 and 3 and to peptides SEQ ID NOs: 4 and 5, respectively, to elicit outgrowth of peptide-specific CTLs. The CTLs elicited by these peptides were first shown to lyse LCL targets only in the presence of the peptide used to elicit their outgrowth and only if the cells expressed HLA class I molecules to which the peptides bound. Using such proven CTLs, it was then shown that ME180 human cervical epithelial cells behaved just as did the LCLs. The CTLs lysed ME180 targets only if the peptide used to stimulated the outgrowth of the CTLs was present and only if the ME180 targets expressed the HLA class I molecules to which the peptides bound.

The final demonstration was to show that the CTLs grown out by stimulation with our invention could destroy (i.e. lyse) genital tract epithelial cells actually infected with Ct. For this purpose, we used CTLs that had been elicited by in vitro stimulation with with HLA-A2-presented CTL epitopes (SEQ ID NOs: 2 and 3). ME180 or its HLA-A2-expressing transferent cells were labeled with [$^3$H]uridine, infected with Ct and used as targets for the CTLs. The infected targets were lysed only if they expressed HLA-A2; uninfected cells were not lysed even if they expressed HLA-A2.

In summary, the peptides comprising our invention detect and elicit the outgrowth of CTLs that lyse Ct-infected human genital tract epithelial cells and could well play an important role in clearing Ct infection in vivo.

Diagnostic Protocols

It will be appreciated that instead of using known blood samples, samples from subjects whose infection status is not known can be tested via the above techniques. An example protocol for a diagnostic test is as follows.

The ability to detect MOMP peptide-specific CTLs is in a human subject indicates that a previous infection with Ct or an immunization, e.g. with a MOMP-based vaccine, was able to induce CTL responses in that person.

Once one knows HLA class I-presented peptide epitopes specifically recognized by CTLs, an extremely sensitive and specific method to detect peptide-specific CTLs is available, thanks to the development of HLA class I tetramers as described in J. Altman et al., 274 Science 94–96 (1996). Tetramers are soluble reagents formed by four identical HLA class I molecules folded in vitro with a synthetic peptide that corresponds to a CTL epitope presented by the specific kind of HLA class I molecule comprising the tetramer.

Tetramers have become a popular reagent for detecting antigen-specific T cells isolated from a variety of sources. By attaching a fluorescent marker to the tetramers, T cells that specifically recognize the peptide used for tetramer folding can easily be detected by flow cytometry.

The MOMP CTL epitopes we identified can be used to create such HLA class I tetramers, for use in diagnostic tests. For example, we have made HLA-A2 tetramers folded with two of the claimed sequences (SEQ ID NOs: 2 and 3) and successfully used the reagents to detect MOMP CTLs in the peripheral blood of Ct-infected people. This also confirmed our interesting novel finding that CTLs specific for our sequences indeed exist in vivo.

CD8+ cells of HLA-A2+ STD subjects were stimulated in vitro with the peptides SEQ ID NOs: 2 and 3 and stained with tetramers at indicated time points. Staining is specific. T cells cultures stimulated with the two peptides were stained by the corresponding tetramers. T cells that were stimulated with HLA-B62-presented epitope (SEQ ID NOs: 6) were not stained by either of these tetramers.

Tetramers can detect CTLs present at a very low frequency in fresh peripheral blood and one does not have to do in vitro stimulation to be able to detect such CTLs. Despite the low frequencies of tetramer-binding T cells in freshly drawn blood samples, we have studied multiple HLA-A2$^+$ infected subjects and found that these low frequencies were always higher than the "background" frequencies of T cells that bind the A2 tetramers in HLA-A2$^-$ infected subjects or in uninfected HLA-A2$^+$ subjects.

Ct genital tract infections can follow different courses and have pathological sequelae that differ in severity among infected individuals. Tetramers made with the peptides comprising our inventions (SEQ ID NOs: 1–8) will be valuable tools for monitoring the numbers of MOMP-specific CTLs in various body locations, e.g. peripheral blood and genital tract epithelial cells. Such diagnostic determinations made with the invention will provide valuable information that could not be obtained so readily by other means concerning the relations between CTL numbers and locations, on the one hand, and clearance of infections or pathogenesis, on the other. HLA class I tetramers formed with MOMP CTL epitopes will also be valuable for monitoring the outcome of the vaccination described below, i.e. to determine whether the vaccination has indeed worked and induced Ct.-specific immune responses. If the vaccine has worked, one should be able to use tetramers to detect increasing frequencies of MOMP CTLs following immunization.

Vaccine Protocol-A

In a sterile dropper bottle, the suspending medium is sterile phosphate-buffered saline. Some or all of SEQ ID NOs: 1–8 is present at 4 mg/ml. Cholera toxin subunit B at 2 mg/ml is also present to enhance immune responses at mucosal surfaces, which are the sites at which Ct multiply and cause pathology. Use of subunit B has been safely tested with humans in other contexts.

To administer to a human, one shakes well, and uses two drops (about 0.1 ml) in each nostril and each eye. Administration should preferably be on days 0, 7 and 14. T- and/or B- cell epitope peptides may also optionally be included, as may booster applications.

Vaccine Protocol-B

The proposed vaccine agent is an attenuated bacterial strain of Salmonella typhimurium bearing a replicating plasmid into which is inserted DNA sequences capable of expressing the peptides of interest in vivo. We propose as a vector attenuated *Salmonella typhimurium* strain $_{xo}4072$. See F. Schödel et al., 62 Infect. and Immun. 1669–1676 (1994) which has A crp-1 and Δ cya mutations that render it avirulent and a Δ asdA-1 mutation that renders it inviable unless a normal asdA gene is present on an indwelling plasmid.

Plasmid PYAN is a form of pYA292 that is modified to have a Nco I site. See Schodel et al., supra. The presence of the Nco I site allows in frame insertion of the AUG of the foreign protein of interest into the plasmid. PYAN lacks antibiotic resistance genes, allowing use of antibiotics should symptoms suggestive of Salmonella pathology appear.

pYAN does have a normal asdA gene, which maintains viability of only those bacteria that retain the plasmid. A DNA sequence is synthesized encoding an AUG followed by the sequences encoding the peptide. The suggested dose is $5 \times 10^4$ colony forming units for small children and $5 \times 10^5$ colony forming units for adults.

For adults, the bacteria will be administered with sodium bicarbonate (2 g of $NaHCO_3$ in 150 ml of distilled water). One should first drink 120 ml of the solution to neutralize gastric acid. One minute later, one drinks the remaining 30 ml of bicarbonate solution, now containing the bacteria. No food or drink is permitted for 90 minutes before or after vaccination.

Vaccine Protocol-C

Alternatively, the DNA may be delivered by other DNA delivery techniques e.g. with a "gene gun" in which the DNA is adsorbed to microscopic gold particles that are propelled into skin cells of vaccinees by a pulse of high pressure helium. The invention has three features that make it especially suitable for use in DNA vaccines.

(1) MOMP peptide 249–268 contains five known human CTL epitopes and six known T helper cell epitopes; this 20-mer has the highest density of human T cell epitopes that has been reported for any antigen. Thus, quite a short segment of DNA can elicit CTL responses to multiple CTL epitopes.

(2) Our CTL epitopes overlap T helper cell (Th) epitopes. Th cells secrete various cytokines, which facilitate the generation and long-term maintenance of CTL responses. Indeed, accumulating experience with DNA vaccines, including some delivered with the gene gun, indicates that CTL responses are enhanced when the vaccine DNA encodes Th cell epitope(s). This juxtaposition of the two kinds of epitopes is observed with all eight of our CTL epitopes. It exists for epitopes located in MOMP segment 249–268, but note also that the isolated CTL epitopes SEQ ID NOs. 1, 4 and 5 overlap Th epitopes that are located in peptides 89–105, 157–175 and 344–359, respectively. Thus, DNA segments encoding each of our CTL epitopes would also encode Th epitopes, increasing the chances that responses to the CTL epitopes would be enhanced by the Th epitopes.

(3) Our CTL epitopes in aggregate are presented with four different kinds of HLA class I molecules (HLA-A2, -B35, -B51 and -B62). Thus, their use as vaccine components should elicit immune responses to one or more CTL epitopes in a large proportion of the population. This versatility of the vaccine is increased by the fact that diverse HLA class II (DR) molecules present to the immune system the Th epitopes that overlap the CTL epitopes. This increases the chance that the CTL responses will be enhanced by the Th responses elicited by the same DNA fragment.

In all three respects set out above, our invention is unique with regard to human CTL epitopes in Ct MOMP.

While the preferred embodiments have been described above, it will be appreciated by those skilled in the art that other modification can be made within the scope of the invention. For example, instead of expressing the DNA in *E. coli*, one might optimize the DNA for other hosts and express it in those hosts.

Further, while six specific sequences have been identified, it is believed that the techniques of the present invention can be utilized to identify other desired 8–10 mers having desirable CTL activation characteristics. Thus, the claims should be looked to in order to judge the full scope of the invention.

Industrial Applicability

The invention provides peptides and DNA that can be used for diagnostic and vaccination purposes.

---

We claim:

1. A purified peptide of 9 to 10 amino acid residues that activates cytotoxic T-lymphocytes, the pelptide comprising an amino acid sequence of SEQ ID NO: 7, wherein the peptide does not have more than 10 amino acid residues.

2. A purified peptide of 9 to 10 amino acid residues that activates cytotoxic T-lymphocytes, the peptide comprising an amino acid sequence of SEO ID NO: 8, wherein the peptide does not have more than 10 amino acid residues.

* * * * *

UNITED STATES PATENT AND TRADEMARK OFFICE
CERTIFICATE OF CORRECTION

PATENT NO.    : 6,225,443 B1
DATED         : May 1, 2001
INVENTOR(S)   : Robert I. DeMars; Seon-Kyeong Kim It is certified that error appears in the above-identified patent and that said Letters Patent is hereby corrected as shown below:

Column 8,
Line 6, replace [BLA] with HLA.

Column 11,
Line 20, replace [A crp-1] with Δ crp-1.
Lines 24 and 27, replace [PYAN] with pYAN.
Line 25, replace [Schodel] with Schödel.

Claim 1,
Line 1, replace [pelptide] with peptide.

Claim 2,
Line 3, replace [SEO] with SEQ.

Signed and Sealed this

Thirteenth Day of November, 2001

Attest:

NICHOLAS P. GODICI
*Attesting Officer*   *Acting Director of the United States Patent and Trademark Office*